United States Patent [19]

Mitchell et al.

[11] Patent Number: 5,002,755

[45] Date of Patent: Mar. 26, 1991

[54] METHOD OF CONTROLLING NEPHROTOXICITY OF ANTI-TUMOR PLAINTUM COMPOUNDS

[75] Inventors: William M. Mitchell; Mark M. Jones; Mark A. Basinger, all of Nashville, Tenn.

[73] Assignee: Vanderbilt University, Nashville, Tenn.

[21] Appl. No.: 344,487

[22] Filed: Apr. 24, 1989

Related U.S. Application Data

[63] Continuation of Ser. No. 157,372, Feb. 18, 1988, abandoned, which is a continuation-in-part of Ser. No. 769,157, Aug. 23, 1985, abandoned.

[51] Int. Cl.$^5$ ..................... A61K 49/00; A61K 33/24; A61K 31/28
[52] U.S. Cl. ..................................... 424/10; 424/649; 514/492
[58] Field of Search ................... 424/10, 649; 514/492

[56] References Cited

U.S. PATENT DOCUMENTS 4,426,372  1/1984  Borch .................................... 424/10

OTHER PUBLICATIONS

Juckett et al., Am. Assoc. Cawc. Res. Proc. (1984) 25:322 (Abst 1274) and (1985) 373 (Abst 1472).
Shiwobu et al., Acta Pharmacol. et Toxicol (1984) 54:189–194.

*Primary Examiner*—Jerome D. Goldberg
*Attorney, Agent, or Firm*—Reising, Ethington, Barnard, Perry & Milton

[57] ABSTRACT

Nephrotoxicity of anti-tumor platinum coordination compounds (e.g., cisplatin) is reduced by administering a dithiocarbamate chelator (e.g., diethyldithiocarbamate) at least 12 hours before as well as immediately after the administration of the anti-tumor compound.

15 Claims, No Drawings

METHOD OF CONTROLLING NEPHROTOXICITY OF ANTI-TUMOR PLAINTUM COMPOUNDS

RELATED APPLICATION

This application is a continuation of pending application Ser. No. 157,372, filed Feb. 18, 1988, now abandoned which was a continuation-in-part of co-pending application Ser. No. 769,157, filed Aug. 23, 1985, now abandoned.

FIELD OF INVENTION

The field of this invention is the administration of anti-tumor platinum compounds to human patients. The invention is particularly concerned with the use of dithiocarbamate chelators to reduce nephrotoxicity of the platinum compounds.

BACKGROUND OF INVENTION

Cisplatin (diamminedichloroplatinum) is currently a standard therapy for testicular and ovarian tumors despite its renal toxicity. Since the toxicity is dose-related, the use of increased doses against other human cancers is restricted.

Research efforts have been directed to finding cisplatin analogs of reduced toxicity while remaining effective as anti-cancer agents. To date, however, no other platinum compound has been approved for general clinical use.

Research efforts have also been directed to finding metal chelating agents which when administered with cisplatin exhibit a renal-sparing effect. The most successful of these chelators is diethyldithiocarbamate (DDTC). See Borch et al. *Proc. Natl. Acad. Sci. U.S.A.* (1979) 76:6611-6614; and Walker et al., *Annals Clin. & Lab. Sci.* (1981) Vol. II, pp. 397-410. Recently it has been reported that certain hydroxylated dithiocarbamates such as dihydroxyethyl dithiocarbamate may provide an improvement over DDTC in reducing nephrotoxicity. Juckett et al., *Am. Assoc. Canc. Res. Proc.* (1984) 25:322 (ABST 1274); and (1985) 373 (ABST 1472).

The original experiments of Borch et al. (1979, cited above) utilized post-administration of DDTC, the dithiocarbamate inhibitor being given from 1 to 4 hours after the start of the administration of the cisplatin. *Proc. Natl. Acad. Sci. U.S.A.* (1980) 77:5441-5444.

A more extensive study of administration times for DDTC was carried out by Gale et al., *Annals Clin & Lab. Sci.* (1982) 12:345-355. These researchers tested DDTC administration 30 minutes before cisplatin administration, and 30 minutes, 1 hour, 2 hours, 4 hours, and 6 hours after the start of administration. They concluded: "When DDTC was given 0.5 hours prior to cisplatin, there was excellent protection from the toxic effects of cisplatin. Optimum therapeutic efficiency was obtained when DDTC was given 1 to 2 hours after cisplatin." Juckett et al. (1984 and 1985, cited above) administered the dithiocarbamates around the time of cisplatin infusion, the earliest time being 30 minutes prior.

As far as is known, no administration protocol has been described for any dithiocarbamate chelator which entirely suppresses an effect on renal function, as measured by blood urea nitrogen (BUN) and creatinine values. In prior art methods, BUN values remained substantially elevated despite the co-administration of a dithiocarbamate chelator. There has been a recognized need to provide more effective renal sparing to permit cisplatin to be administered in larger doses, and/or used for a wider range of cancer therapy

SUMMARY OF INVENTION

This invention is based in part on the discovery that a markedly improved renal sparing effect is obtained by administering the dithiocarbamate chelator 12 hours or more prior to the start of the cisplatin administration. This is surprising. It would have been assumed that such early administration of DDTC would have had little residual effect. The method of the present invention, therefore, marks a sharp departure from prior practice in which the dithiocarbamate chelator was administered essentially concurrently with the cisplatin.

The theoretical explanation for the improved control of nephrotoxicity provided by the present invention is not known. The early administration appears to have a sensitizing or preconditioning effect. It does not function in the same way as the latter administration. During the experiments which led to the present invention, it was found that the early administration of the dithiocarbamate had no appreciable renal sparing effect unless the early administration was accompanied by a later administration concurrent with the cisplatin administration. This finding is also considered surprising. It was found that the combination of early and concomitant administrations provides a major improvement over concomitant administration alone. The improvement obtained is such that the renal function can be almost completely spared as measured by BUN and creatinine values without decreasing the antitumor activity of cisplatin.

DDTC and other known analogs thereof, such as di(hydroxyethyl) dithiocarbamate, can be employed in either or both of the administration steps of this invention, it is preferred to employ sodium N-methyl, N-dithiocarboxy-D-glucamine (NGDTC) in both administrations, or at least in the concurrent administrations. It is believed that the use of NGDTC is particularly beneficial in the second administration of the dithiocarbamate. To our knowledge NGDTC has not been reported by any other investigator as being of value as a renal sparing agent for cisplatin.

DETAILED DESCRIPTION

The method of this invention can be practiced with any anti-tumor platinum coordination compound which are water-soluble and provide the platinum in the form of an ion having anti-tumor activity. Such ionic forms of platinum are understood to have a chelating-type reaction with dithiocarbamates. Clinically, the compound known as cisplatin represents the established therapy, but several dichloro-analogs are known for the parent compound, now called cisdichlorodiammine platinum (II). Other analogs also having anti-tumor activity are known A number of such analogs are pending for clinical use approval Among the anti-tumor platinum coordination compounds described in the literature which are believed to be useable with the method of this invention are: trans-diaminidichloroplatinum(II), cis-diamminiediaquaplatinum(II)-ion, chloro(diethylenetriamine)-platinum(II) chloride, dichloro (ethylenediamine)-platinum(II), diammine(1,1-cyclobutanedicarbxxylato)platinum(II) (Carboplatin), (Spiroplatin), (Iproplatin), diammine(2-ethylmalonato)- platinum(II), ethylenediaminemalonatoplatinum(II), aqua(1,2-diaminodyclohexane)-sulfatoplatinum(II), (1,2-diaminocyclohexane) malonatoplatinum(II), (4-carboxyphthalato) (1,2-diaminocyclohexane) platinum-(II), (1,2-diaminocyclohexane)-(isocitrato) platinum(II), (1,2-diaminocyclohexane) cis (pyruvato) platinum(II), and (1, 2-diaminocyclohexane)-oxalatoplatinum(II). Until other anti-tumor platinum compounds are approved for clinical use, however, cis-platin is preferred for practicing the method of the present invention.

The method of this invention is believed to be usable with any dithiocarbamate chelator which has a renal-sparing effect when administered with a platinum compound. Such compounds as diethyldithiocarbamate (DDTC) and analogs thereof, including particularly hydroxylated analogs, such as di(hydroxyethyl)dithiocarbamate (HDTC). A preferred compound for use in practicing the method of this invention is N-methyl, N-dithiocarboxy-D-glucamine (NGDTC).

The anti-tumor platinum compound can be administered in the same manner as in prior clinical practice. More specifically, slow intravenous infusion is the method of choice. For example, an administration protocol may be used like that described by Chary et al., Cancer Rep. (1977), 61:367-370. The cisplatin is intravenously infused. For promoting diuresis the incorporation of mannitol in a dextrose/saline is the preferred carrier. The protocol can also include prehydration of the patient by administration of a dextrose/saline solution before the cisplatin. The dose schedule of cisplatin may be on the basis of 1 mg per kg of body weight or 60 mg per square meter of body surface. Infusions may be given one to two times weekly, and the weekly treatments repeated several times unless renal toxicity provides a contraindication.

One critical factor in practicing the present invention is the time of the first administration of the dithiocarbamate chelator. The dithiocarbamate in the form of a water-soluble salt should be given at least 12, and preferably at least 20 hours before the start of the administration of the platinum compound. The dithiocarbamate chelator is preferably in the form of its sodium salt, but other water-soluble salts of non-toxic cations can be employed, such as an ammonium salt. A general time range for the first administration of the dithiocarbamate is from 12 to 36 hours, or preferably from 20 to 28 hours prior to the platinum administration. Good results have been obtained with a 24-hour prior administration.

For the initial administration of the dithiocarbamate chelator, at least 5 and preferably at least 25 milligrams (mgs) should be given per kilogram (kg) of the patient's body weight. Since the initial dosage appears to act as a preconditioner for the subsequent administration, it is believed that a smaller amount of the chelator will be effective for the initial administration. It is believed to be unnecessary to employ more than 500 mgs of the dithiocarbamate chelator for the first administration per kg of patient body weight Substantially optimized results are believed to be obtainable in the range of 25 to 100 mgs/kg body weight for the first administration. However, larger amounts of the dithiocarbamate chelator can be administered in the first administration without deleterious effect. The chelator itself is relatively non-toxic.

For the first administration, parenteral administration intravenous injection or intravenous infusion is preferred. However, other routes of administration can be employed, including oral or intraperitoneal. Dithiocarbamate chelators are rapidly absorbed into the bloodstream from the intestines or peritoneal cavity. Since the first administration is many hours prior to the platinum administration, a delay in the absorption into the bloodstream is acceptable. However, intravenous infusion is desirable. The dithiocarbamate chelator can be dissolved in a carrier solution such as normal saline, 5% glucose, or mixtures thereof.

The second administration of a dithiocarbamate chelator is carried out as in present practice, that is, on a generally concurrent basis with the administration of the platinum compound. More specifically, the second administration of the chelator can be carried out in a time period from 0.5 hours before to 4.0 hours after the administration of the platinum compound. A preferred administration schedule is from the start of the platinum administration to about 1 to 2 hours later. The amount of the dithiocarbamate chelator to be given in the second administration can be in accordance with present practice At least from 50 to 200 milligrams (mgs) of the chelator should be given per kilogram (kg) of patient body weight. A broader range is from 100 to 1000 mgs/kg body weight An effective range is from 200 to 800 mgs/kg body weight.

Previously used dithiocarbamate chelators can be employed in the second administration step, such as particularly DDTC and HDTC. It is believed, however, that the most desirable chelator in the second step is the compound N-methyl, N-dithiocarboxy-D-glucamine (NGDTC). A test of NGDTC for cadmium intoxication has heretofore been reported See Shinobu et al., Acta Pharmacol. et Toxicol. (1984) 54:189-194. The highly hydroxylated form of NGDTC improves its water solubility and promotes its elimination from the body. NGDTC may also be used in the early administration. It will usually be convenient to employ the same chelator compound for both steps.

Other accepted practices can be employed in conjunction with the cisplatin administration. For example, acetazolamide may be given in normal saline prior to the cisplatin. This use of acetazolamide is described by Osman et al., Cancer Rep. (1984) 68:999-1004.

For the second administration, the route of choice is intravenous infusion. The dithiocarbamate chelator can be given in the same solution as the platinum compound. The administration of the dithiocarbamate chelator may be carried out over the first one to two hours of the platinum administration.

EXPERIMENTAL EXAMPLES

In the following experiments, the rat was selected as the experimental animal as a known model for human response to the nephrotoxicity of cisplatin. See Guarino et al., Cancer Tret. Rep. (1979) 63:1475-1483. Guarino et al. confirmed that the rat was a satisfactory model with respect to cisplatin analogs. Elevations of blood urea nitrogen (BUN) and creatinine were employed as a criterion of impairment of renal function in accordance with the practice of prior investigators. See, for example, Goldstein et al., Toxicol.& Appl. Pharmacol. (1981) 60:163-175.

EXAMPLE I

Materials and Methods

Cisplatin and DDTC were obtained from commerical sources, since they are generally available in the U.S. N-methyl, N-dithiocarboxy-D-glucamine (NGDTC)

was prepared by the method described in Shinobu et al., *Acta Pharmacol. et Toxicol.* (1984) 54:189-194.

Blood urea nitrogen (BUN) and creatinine determinations were performed using male, F344 rats (average weight 160 g), obtained from Harlan Industries, Indianapolis, IN. Tumor response studies were carried out using female Sprague-Dawley rats (average weight 165 g), also obtained from Harlan Industries. The animals were allowed a four day acclimation period after shipment before being used experimentally. Food and tap water were allowed ad libitum.

Both BUN and creatinine values were determined utilizing IL Urea Nitrogen Kit No. 3516 and IL Creatinine Test Kit No. 35164 of Sigma Chemical Co., St. Louis, MO. These determinations were performed using an automated centrifugal analyzer.

Blood samples for all determinations were obtained from the tip of the tail while the animal was under light ether anesthesia. After BUN and creatinine analyses were completed animals were sacrificed by cervical dislocation, the kidneys removed and placed in 10% buffered formalin, embedded in paraffin, sectioned, and stained with hematoxylin and eosin for histopathological examination.

Platinum levels were determined using flameless atomic absorption spectrophometry, and using standard operating parameters with deuterium arc background correction. Samples were wet washed in nitric acid, the acid evaporated at 140, and the samples brought to volume using distilled water.

Tumor response studies were performed using the standard Walker 256 carcinoma (ATCC CCL38). The induction of tumor growth was achieved by inoculating test animals with a cell suspension containing $10^6$ tumor cells subcutaneously at two sites in the axillary region for tumor response assessment. This cell suspension was obtained by removing tumors from animals which had been inoculated eight days earlier, placing the tumors in saline, mincing, and passing the tumor through a 50 mesh cell sieve. Inoculations were 0.3 ml in volume at each site. After being inoculated, the animals were randomly divided into experimental treatment groups as described in the text. Palpable tumors were noted on day three following inoculation at which time treatment was started. All animals were sacrificed on day nine following tumor inoculation, the tumors excised, measured and weighed.

All injectate solutions for both BUN and creatinine experiments and for the tumor response experiments were prepared in normal saline just prior to use. Cisplatin was administered at a level of 7.5 mg/kg via tail vein injection. Cisplatin solutions contained cisplatin at a concentration of 20 mg/ml. Acetazolamide was administered subcutaneously at a level of 20 mg/kg (15). DDTC and NGDTC were administered intraperitoneally at indicated levels and concentrations.

Results

The following Tables A and B summarize the treatment regimens and the results obtained with each regimen. Table A reports the blood urea nitrogen (BUN) value and the creatinine values (shown in) at day 5, 10 and 15, and the renal platinum values at day 15. Table B reports measurements on the tumors of weight and size together with BUN and creatine values determined on day 9 when the animals were sacrificed. The treatment regimens are summarized for each group of the tables.

Results of these tests clearly demonstrate the value of the combined early and concomitant administrations of the dithiocarbamate chelators. The low BUN values of test groups 5, 6 and 7 compare with the much higher BUN values of groups 3 and 4 that do not include the 24 hour prior administration of the DDTC. The lowest BUN values were obtained with group 6, where DDTC was administered 24 hours prior to NGDTC was administered 1 hour and 3 hours after the cisplatin. Those values appear to be at substantially normal BUN levels, for example, as indicated for group 1 in Table B.

The data of Table B demonstrates that the improved renal sparing is not obtained at the expense of antitumor activity. The 24 hours pretreatment with DDTC and concomitant treatment with NGDTC of groups 5 and 6 still produced approximately the same tumor regression as measured by tumor weight and size.

TABLE A

Chelator effects on inhibition of Cis-PT induced renal toxicity and residual platinum renal concentration

| Group No. | Treatment regimen[a] | N | Blood urea nitrogen (creatinine) Day 5 | Day 10 | Day 15 | Renal Platinum at day 15 reported as ppm/wet weight (gm) |
|---|---|---|---|---|---|---|
| 1 | Control Cisplatin (7.5 mg/kg) | 5 | 133.4 ± 16.8 (3.10 ± 0.32) | 73.6 ± 14.4 (1.16 ± 0.27) | 51.6 ± 8.4 (0.9 ± 0.1) | 9.2 ± 0.6 |
| 2 | Pretreat with physiological saline 3 ml at −30 min (saline substituted for antidote vol.) | 6 | 89.3 ± 13.2 (2.4 ± 0.42) | 52.4 ± 10.3 (1.1 ± 0.13) | 49.3 ± 4.6 (0.96 ± 0.07) | 9.4 ± 0.6 |
| 3 | Pretreat DDTC[b] 50 mg/kg − 1 hr Acetazolamide 20 mg/kg −30 min DDTC 362 mg/kg +1 hr, +3 hr | 3 | 83.7 ± 19.0 (1.68 ± 0.23) | 47.6 ± 8.3 (0.87 ± 0.06) | 51.5 ± 7.0 (0.08 ± 0.1) | 2.7 ± 0.2 |
| 4. | Pretreat DDTC 50 mg/kg −1 hr Acetazolamide 20 mg/kg −30 min NGDTC[b] 500 mg/kg +1 hr, +3 hr | 6 | 31.7 ± 4.9 (0.78 ± 0.03) | 40.5 ± 3.2 (0.83 ± 0.05) | 33.3 ± 3.7 (0.82 ± 0.12) | 4.5 ± 1.2 |
| 5 | Pretreat DDTC 50 mg/kg −24 hr Acetazolamide 20 mg/kg −30 min NGDTC 500 mg/kg +1 jr, +3 hr | 6 | 23.0 ± 5.6 (0.77 ± 0.06) | 25.3 ± 3.8 (0.77 ± 0.04) | 25.4 ± 2.6 (0.75 ± 0.02) | 2.4 ± 0.2 |
| 6 | Pretreat DDTC 500 mg/kg −24 hr Acetazolamide 20 mg/kg −30 min NGDTC 500 mg/kg +1 hr, +3 hr | 3 | 22.2 ± 4.1 (0.80 ± 0.05) | 29.2 ± 4.5 (0.80 ± 0.04) | 26.8 ± 1.3 (0.78 ± 0.01) | 3.5 ± 0.4 |
| 7 | Pretreat DDTC 50 mg/kg −24 hr Acetazolamide 20 mg/kg −30 min | 3 | 29.8 ± 2.9 (0.86 ± 0.04) | 33.6 ± 1.9 (0.89 ± 0.03) | 29.3 ± 0.9 (0.76 ± 0.08) | 3.9 ± 0.7 |

TABLE A-continued

Chelator effects on inhibition of Cis-PT induced renal toxicity and residual platinum renal concentration

| Group No. | Treatment regimen[a] | N | Blood urea nitrogen (creatinine) Day 5 | Day 10 | Day 15 | Renal Platinum at day 15 reported as ppm/wet weight (gm) |
|---|---|---|---|---|---|---|
| | DDTC 500 mg/kg +1, +3 hr | | | | | |

[a] Cis-Pt administered iv at time 0. All antidotes given ip at stated time relative to Cis-Pt.
[b] DDTC = sodium diethyldithiocarbamate.
NGDTC = sodium N-methyl, N-dithiocarboxy-D-glucamine.

TABLE B

Antitumor activity of Cis-Pt as a function of chelator induced renal sparing

| Group No. | Treatment regimen[a] | N | Tumor[b] weight (gm) | size (mean) diameter | BUN[b] | Creatinine[b] |
|---|---|---|---|---|---|---|
| 1 | None | 6 | 4.8 ± 1.2 | 2.2 ± 0.4 | 22.0 ± 2.0 | 0.82 ± 0.06 |
| 2 | Cisplatin (7.5 mg/kg) | 6 | 0.2 ± 0.1 | 0.7 ± 0.1 | 173 ± 64 | 3.3 ± 2.7 |
| 3 | DDTC (50 mg/kg) −24 hr acetazolamide (20 mg/kg) −30 min DDTC (360 mg/kg) +1 hr +3 hr | 6 | 0.3 ± 0.1 | 0.8 ± 0.2 | 65 ± 36 | 1.1 ± 0.4 |
| 4 | NGDTC[c] (500 mg/kg) +1 hr, +3 hr | 6 | 0.2 ± 0.2 | 0.8 ± 0.2 | 50 ± 20 | 1.0 ± .1 |
| 5 | DDTC (50 mg/kg) −24 hr Acetazolamide (20 mg/kg) −30 min NGDTC (500 mg/kg) +1 hr, +3 hr | 6 | 0.3 ± 0.2 | 0.8 ± 0.2 | 28 ± 8 | 0.8 ± 0.1 |
| 6 | NGDTC (70 mg/kg) −24 hr Acetazolamide (20 mg/kg) −30 min NGDTC (500 mg/kg) +1 hr, +3 hr | 5 | 0.2 ± 0.1 | 0.7 ± 0.2 | 31 ± 12 | 1.0 ± 0.1 |

[a] Cisplatin administered iv at time 0 to all groups except group No. 1.
[b] Animals sacrificed at day 9 following tumor inoculation.
[c] DDTC = sodium diethyldithiocarbamate.
NGDTC = sodium N-methyl, N-dithiocarboxy-D-glucamine.

EXAMPLE II

The method of the present invention was followed in a comparative procedure with the method of the Borch U.S. Pat. No. 4,426,372.

Materials and Methods

In the comparative tests, male Fischer F344 rats (average weight 165±6 gms) were obtained from Sasco, Inc., Indianapolis, IN. They were divided into groups of three, five and six rats, placed in cages, and given Wayne Lab Blocks and water ad lib. They were acclimated to the environment for seven days. Average weight of the rats was 165+6 gm when injected.

All solutions were prepared just prior to administration in isotonic saline (0.9% sodium chloride NaCl). The DDTC was prepared at a concentration of 265 mg/ml; Acetazolamide was prepared at a concentration of 1 mg/ml. The NaG was prepared at a concentration of 370 mg/ml. The DDTC, Acetazolamide and NaG were prepared in accordance with the procedures described in the pending patent application. The cisplatin was administrated at a concentration of 2 mg/ml and is identified by the trademark PLATINOL, manufactured by Bristol Labs, Syracuse, New York 13201. Blood was obtained from the tail vein for serial BUN (Blood Urea Nitrogen)/creatinine determinations at 5 days after injection, reportedly the time of maximal observed toxicity.

Antidote solutions of the chelators were prepared so that 0.6 ml was administered per 160 grams of g/body weight.

The chelators were administered at various times before and after the administration of the platinum compound, ranging from 24 hours before administration in accordance with the present invention and up to 30 minutes before administration in accordance with the Borch disclosure. After administration dosage times were noted at 1 and 3 hours.

Results

As shown in Table C, at day 5, BUN/creatinine levels for rats that were administered the chelator at 30 minutes before administration of the platinum compound were quite high, with a reading of about 49.2 mg per dl. Those animals that received the chelator 24 hours before administration of the platinum compound had significantly lower BUN/creatinine levels at day 5. The reduction in BUN/creatinine levels at day 5 indicates the beneficial effects in reducing nephrotoxicity. Table D shows the survival data of animals used in another experiment where cisplatinum was prepared in distilled water. As noted, no animals survived the dose of the platinum compound that received the chelator 30 minutes before administration of the platinum compound. It can be seen from this comparative study that the method of the present invention reduced nephrotoxicity in mammals administered cisplatinum.

TABLE C

| Treatment[1] | Amount[2] | Method of Administration[4] and Time | | Day 5 BUN/Creatinine |
|---|---|---|---|---|
| DDTC | 50 mg/kg | ip | −30 min | |
| Acetazolamide | 20 mg/kg | sc | −30 min | |
| Cis-Pt | 7.5 mg/kg | iv | 0 | N = 3   49.2 ± 1.1/1.3 ± .26 |
| DDTC | 500 mg/kg | ip | 1 hr, 3 hr | |
| DDTC | 50 mg/kg | ip | −24 hr | |
| Acetazolamide | 20 mg/kg | sc | −30 min | |
| Cis-Pt | 7.5 mg/kg | iv | 0 | N = 3   27.4 ± 3.1/.93 ± .06 |
| DDTC | 500 mg/kg | ip | 1 hr, 3 hr | |
| DDTC | 50 mg/kg | ip | −24 hr | |
| Acetazolamide | 20 mg/kg | sc | −30 min | |
| Cis-Pt | 7.5 mg/kg | iv | 0 | N = 3   35.1 ± 7.3/1.03 ± .06 |
| NaG | 500 mg/kg | ip | 1 hr, 3 hr | |
| Cis-Pt[3] | 7.5 mg/kg | iv | 0 | N = 5   133.4 ± 16.8/3.1 ± .32 |

[1]DDTC = sodium diethyldithiocarbamate; Cis-Pt - cisplatin; and NaG = N-dithiocarboxy-D-glucamine.
[2]All solution were prepared just prior to administration in .9% normal saline. Acetazolamide was prepared at a concentration of 1 mg/ml. Cis-Pt was administered at a concentration of 2 mg/ml and was of the same type used clinically (Bristol Labs, Syracuse, NY, 13201). Antidote solutions were prepared so that .6 ml was administered per 160 g/body weight.
[3]Jones, et al., Cancer Chemotherapy Pharmacol (1986), 17:38–42.
[4]ip = intraperitoneal; sc = subcutaneous; and iv = intravenous.

TABLE D

| Treatment[1] | Amounts | Method of Administration[2] and time | | Survival/Total |
|---|---|---|---|---|
| DDTC | 50 mg/kg | ip | −30 min | 0/6 |
| Acetazolamide | 20 mg/kg | sc | −30 min | |
| Cis-Pt | 7.5 mg/kg | iv | 0 | |
| DDTC | 500 mg/kg | ip | 1 hr, 3 hr | |
| DDTC | 50 mg/kg | ip | −24 hr | 5/6 |
| Acetazolamide | 20 mg/kg | sc | −30 min | |
| Cis-Pt | 7.5 mg/kg | iv | 0 | |
| DDTC | 500 mg/kg | ip | 1 hr, 3 hr | |
| DDTC | 50 mg/kg | ip | −24 hr | 5/6 |
| Acetazolamide | 20 mg/kg | sc | −30 min | |
| Cis-Pt | 7.5 mg/kg | iv | 0 | |
| NaG | 690 mg/kg | ip | 1 hr, 3 hr | |
| *Cis-Pt | 7/5 mg/kg | iv | 0 | 5/6 |

[1]DDTC = sodium diethyldithiocarbamate; Cis-Pt = cisplatin; and NaG = N-methyl, N-dithiocarboxy-D-glucamine.
[2]ip = intraperitoneal; sc = subcutaneous; and iv = intravenous
*Cis-Pt was prepared in distilled H$_2$O and was of the same sort used in previous experiments (Bristol Labs, Syracuse, NY 13201).

EXAMPLE III

A further comparative experiment was conducted in accordance with the procedures of Example II. Acetazolamide was not used, a dithiocarbamate chelator (DDTC) was administered 12 hours prior to the platinum compound (Cis-Pt), and a second dithiocarbamate chelator (NaG) was administered at 1 and 3 hours after the Cis-Pt. The data is summarized in Table E. The data shows that the method of this invention provided improved protection against nephrotoxicity. Both the BUN and creatinine levels were improved. The same amount of Cis-Pt (7.5 mg/kg) was administered without the use of any chelator, BUN/creatinine levels were respectively 24.6±12.7/6.5±1.2, and only two of the six rats survived.

TABLE E

| Treatment[1] | Amounts | Method of Administration[2] and Time | | Day 5 BUN/Creatinine |
|---|---|---|---|---|
| DDTC | 50 mg/kg | ip | −12 hr | |
| Cis-Pt | 7.5 mg/kg | iv | 0 | |
| NaG | 500 mg/kg | ip | +1 jr, +3 hr | 100.2 ± 14.1/1.8 ± 0.6 |
| DDTC | 50 mg/kg | ip | −0.5 hr. | |
| Cis-Pt | 7.5 mg/kg | iv | 0 | |
| DDTC | eg. mol. to 50 mg/kg of NaG[3] | ip | +1 hr, +3 hr. | 137.7 ± 32.8/3.5 ± 0.8 |

[1]DDTC = sodium diethyldithiocarbamate; Cis-Pt = cisplatin; and NaG = N-methyl, N-dithiocarboxy-D-glucamine.
[2]ip = intraperitoneal; sc = subcutaneous; and iv = intravenous
[3]DDTC was given in a molar equivalent amount to 500 mg/kg of NaG.

We claim:

1. The method of controlling nephrotoxicity in the treatment of cancer in human patients wherein an effective amount of a water-soluble anti-tumor platinum coordination compound is parenterally administered, comprising;

(a) from 12 to 36 hours prior to the start of the administration of the platinum compound administering to the patient at least 5 and up to 500 milligrams (mgs) of a dithiocarbamate chelator per kilogram (kg) of patient body weight, said chelator compound being in the form of a water-soluble salt of a non-toxic cation, and being selected from the group consisting of diethyldithiocarbamate, di(hydroxyethyl) dithiocarbamate, and N-methyl, N-dithiocarboxy-D-glucamine; and (b) from the start of the administration of the platinum compound to 4.0 hours thereafter administering at least 50 and up to 1,000 milligrams (mgs) of a dithiocarbamate chelator per kilogram (kg) of patient body weight.

2. The method of claim 1 in which said step (a) is carried out from 20 to 28 hours prior to the start of the administration of the platinum compound, and said dithiocarbamate chelator is administered in an amount of 25 to 500 mgs per kg of patient body weight.

3. The method of claim 1 or claim 2 in which said step (b) is carried out within a time period from the start of the administration of said platinum compound to 2 hours thereafter, and said dithiocarbamate chelator is administered in an amount of 200 to 800 mgs per kg of patient body weight.

4. The method of claim 1 or claim 2 in which said platinum compound is cisplatin.

5. The method of claim 1 in which the chelator employed in step (b) is a hydroxylated dithiocarbamate.

6. The method of claim 1 in which said chelator is selected from the group consisting of di(hydroxyethyl) dithiocarbamate and N-methyl, N-dithiocarboxy-D-glucamine.

7. The method of claim 5 or claim 6 in which said hydroxylated dithiocarbamate is in a salt form selected from sodium and ammonium salts.

8. The method of controlling nephrotoxicity in the treatment of cancer in human patients wherein an effective amount of a water-soluble anti-tumor platinum coordination compound is parenterally administered, comprising:
  (a) from 20 to 28 hours prior to the start of the administration of the platinum compound administering to the patient from 25 to 500 milligrams (mgs) of a dithiocarbamate chelator per kilogram (kg) of patient body weight, said chelator compound being selected from the group consisting of the sodium or ammonium salts of diethyldithiocarbamate, di(hydroxyethyl) dithiocarbamate, and N-methyl, N-dithiocarboxy-D-glucamine; and
  (b) within a time period from the start of the administration of said platinum compound to 2 hours thereafter administering from 200 to 800 milligrams (mgs) of said dithiocarbamate chelator per kilogram (kg) of patient body weight.

9. The method of claim 8 in which said platinum compound is cisplatin.

10. The method of claim 8 in which said chelator is selected from the group consisting of di(hydroxyethyl) dithiocarbamate and N-methyl, N-dithiocarboxy-D-glucamine.

11. The method of claim 10 in which said chelator is in a salt from selected from its sodium and ammonium salts.

12. The method of claim 10 or claim 11 in which said platinum compound is cisplatin.

13. The method of controlling nephrotoxicity in the treatment of cancer in human patients wherein an effective amount of cisplatin is parenterally administered, comprising:
  (a) from 20 to 28 hours prior to the start of the administration of the cisplatin administering to the patient from 25 to 100 milligrams (mgs) of a dithiocarbamate chelator per kilogram (kg) of patient body weight, said chelator compound being selected from the group consisting of sodium or ammonium salts of diethyldithiocarbamate, di(hydroxyethyl) dithiocarbamate, and N-methyl, N-dithiocarboxy-D-glucamine; and
  (b) within a time period from the start of the administration of said cisplatin to 2 hours thereafter administering from 200 to 800 milligrams (mgs) of a hydroxylated dithiocarbamate chelator per kilogram (kg) of patient body weight, said hydroxylated dithiocarbamate being selected from the group consisting of di(hydroxyethyl) dithiocarbamate and N-methyl, N-dithiocarboxy-D-glucamine.

14. The method of claim 13 in which said hydroxylated dithiocarbamate employed in step (b) is N-methyl, N-thiocarboxy-D-glucamine.

15. The method of claim 13 in which the dithiocarbamate chelator employed in steps (a) and (b) is N-methyl, N-thiocarboxy-D-glucamine.

* * * * *